United States Patent [19]

Frils, Jr. et al.

[11] 3,984,545

[45] Oct. 5, 1976

[54] NOVEL METHOD AND COMPOSITIONS FOR TREATING PARALYSIS AGITANS

[75] Inventors: Walter Frils, Jr., Bangor; Allan D. Rudzik, Portage, both of Mich.

[73] Assignee: The Upjohn Company, Kalamazoo, Mich.

[22] Filed: Aug. 6, 1975

[21] Appl. No.: 602,321

Related U.S. Application Data

[60] Division of Ser. No. 518,451, Oct. 29, 1974, Pat. No. 3,928,589, which is a continuation of Ser. No. 386,564, Aug. 8, 1973, abandoned.

[52] U.S. Cl. .................................. 424/244; 424/319
[51] Int. Cl.² ................. A61K 31/33; A61K 31/195
[58] Field of Search ........................... 424/319, 244

*Primary Examiner*—Stanley J. Friedman
*Attorney, Agent, or Firm*—John J. Killinger; Roman Saliwanchik

[57] ABSTRACT

An improvement in the method of treating paralysis agitans by administration of 3,4-dihydroxy-phenyl-1-alanine, its hydrates and salts thereof is disclosed, which comprises administering it concurrently with a benzodiazepine compound having sedative-hypnotic and anxiolytic activity. Disclosed also are therapeutic compositions which comprise mixtures of 3,4-dihydroxyphenyl-1-alanine with benzodiazepines. The therapeutic compositions are useful in the treatment of humans afflicted with paralysis agitans.

2 Claims, No Drawings

NOVEL METHOD AND COMPOSITIONS FOR TREATING PARALYSIS AGITANS

This is a division of application Ser. No. 518,451, filed Oct. 29, 1974, now U.S. Pat. No. 3,928,589, which is a continuation of Ser. No. 386,564, filed Aug. 8, 1973, now abandoned.

BACKGROUND OF THE INVENTION

1. Field of the Invention

The invention concerns an improvement in the treatment of humans afflicted with paralysis agitans by administration of 3,4-dihydroxyphenyl-1-alanine. More particularly, the invention concerns potentiation of 3,4-dihydroxyphenyl-1-alanine with a benzodiazepine adjuvant.

2. Description of the Prior Art

A combination of 3,4-dihydroxyphenyl-1-alanine with a tricyclic antidepressant such as 5-[3-(dimethylamino)-propyl]-10,11-dihydro-5H-dibenz[b,f]azepine and an $N^1$-substituted-$N^2$-(2,3-4-trihydroxybenzyl)-hydrazine is disclosed in U.S. Pat. No. 3,646,213 as an effective antidepressant composition.

The use of 3,4-dihydroxyphenyl-1-alanine, hydrates thereof and pharmaceutically acceptable acid addition salts thereof, to treat humans afflicted with paralysis agitans (also referred to alternatively in the literature as "shaking palsy", "Parkinsonism", "Parkinson's syndrome" and "Parkinson's disease") has been well documented; see, for example, Cotzias et al., Long-Term Effects of DOPA on Parkinsonism, 3rd Symposium on Parkinson's Disease, Edinburgh, 1968, Vol. 1, Gillingham and Donaldson, Editors, pps. 178–181, London, E. and S. Livingston, Publ. (1969); DuVoisin et al., 3rd Symposium on Parkinson's Disease, supra., pps. 185–192; Van Woert et al., N. Eng. Jour. Med., 276, 374–9, (1967) and Siegfried et al., Pharm Clin., 2, 23–6, (1969); U.S. Pat. Nos. 3,557,292 and 3,701,829. The dosage of 3,4-dihydroxyphenyl-1-alanine required to alleviate the symptoms of paralysis agitans ranges from 5 to 8 grams daily for the average adult patient. At therapeutic dosage levels, a number of undesirable peripheral side effects occur, such as for example, nausea, involuntary movements (choreiform nods, twitchs, grimaces, weaving gait and shuffles), somnolence, depression and increased libido.

Cash, et al. disclosed in U.S. Pat. No. 3,729,563 that the high doses of 3,4-dihydroxy-1-alanine required to treat Parkinsonism could be reduced by administering it in conjunction with doses of gallic acid. Gallic acid and its derivatives themselves have the property of alleviating involuntary muscle activity for short periods of time.

Siegfried et al., Ger. Med. Monthly, 15, 315, (1970), and Siegfried et al., supra., reported that the dosage of 3,4-dihydroxyphenyl-1-alanine required to alleviate the akinesiatic symptoms of paralysis agitans could be reduced to as little as one-tenth of the usual dosage by administering it in conjunction with a decarboxylase inhibitor (see also J.A.M.A., Vol. 212, No. 11, pg. 1791; U.S. Pat. Nos. 3,557,292 and 3,701,829). Such inhibitors generally block the normal metabolic conversion of dopamine (3,4-dihydroxyphenethylamine) in brain tissue to norepinephrine, thus elevating dopamine levels. Although a number of the peripheral side effects of 3,4-dihydroxyphenyl-1-alanine disappear with reduced dosage levels, the combination with a decarboxylase inhibitor does not provide a completely satisfactory solution for treating paralysis agitans. For example, symptoms of akathisia tend to worsen and tremors seem to become exaggerated (Siegfried et al., Pharm. Clin., supra.). The decarboxylase inhibitors are also not without their limitations in use. For example, they are generally not advisably administered to patients having a history of cardiovascular disease. Since a high proportion of patients afflicted with paralysis agitans also have a history of arteriosclerosis the use of decarboxylase inhibitors to reduce dosage levels of 3,4-dihydroxyphenyl-1-alanine is limited.

We have found that the anti-paralysis agitans symptom activity of 3,4-dihydroxyphenyl-1-alanine is potentiated when administered concurrently with a benzodiazepine compound. As a result, the required dose of 3,4-dihydroxyphenyl-1-alanine for alleviating symptoms of paralysis agitans can be reduced by from 25 to 75 percent with the advantage of reduced side effects.

Our finding is surprising since the benzodiazepines do not themselves bring about a lessening of symptoms of paralysis agitans. Furthermore, the benzodiazepines are not known to inhibit the normal metabolism of dopamine, as occurs with the decarboxylase inhibitors.

The method and compositions of our invention are particularly advantageous because the benzodiazepines are generally not contraindicated in the presence of a history of cardiovascular disease. In addition, we have found the combination of 3,4-dihydroxyphenyl-1-alanine and benzodiazepine to be less toxic than the combination of 3,4-dihydroxyphenyl-1-alanine and a decarboxylase inhibitor such as, for example, imipramine or tranylcypromine or an antidepressant; see for example, Proctor et al., Arch. Int. Pharm., 163, 87, (1966) reporting on the potentiation of lethality of 3,4-dihydroxyphenyl-1-alanine when administered to aggregated mice with monoamine oxidase inhibitors and a similar result obtained when 3,4-dihydroxyphenyl-1-alanine was administered with an antidepressant [Johnson et al., Current Ther. Res., 12, 402, (1970)].

SUMMARY OF THE INVENTION

The invention comprises in the treatment of paralysis agitans by administering a compound selected from 3,4-dihydroxyphenyl-1-alanine, a hydrate thereof and a pharmaceutically acceptable acid addition salt thereof, to a human afflicted with paralysis agitans the improvement which comprises co-administering a potentiating amount of a benzodiazepine compound having sedative-hypnotic and anxiolytic activity.

The invention also comprises a unit dose pharmaceutical composition which comprises an effective amount of a compound selected from 3,4-dihydroxyphenyl-1-alanine, a hydrate thereof and a pharmaceutically acceptable acid addition salt thereof; for treatment of paralysis agitans with a potentiating amount of a benzodiazepine compound in combination with a pharmaceutical carrier. The compositions of the invention are particularly useful for treating humans afflicted with paralysis agitans.

DETAILED DESCRIPTION OF THE INVENTION

The improved method of the invention is carried out by co-administering with a compound selected from 3,4-dihydroxyphenyl-1-alanine, a hydrate thereof and a pharmaceutically acceptable acid addition salt thereof; a potentiating amount of a benzodiazepine having sedative-hypnotic and anxiolytic activity. A potentiating amount is defined to mean that amount which effects a reduction in the amount of 3,4-dihydroxyphenyl-1-alanine, hydrate or salt thereof, required to alleviate the symptoms of paralysis agitans in an afflicted human. In general, a potentiating amount is within the range of from about 0.001 mg./kg. to about 1.0 mg./kg. of body weight of the recipient on a daily basis. Of course, the optimum dosage (potentiating amount) of benzodiazepine compound will be varied according to the specific benzodiazepine compound employed. In general, however, the potentiating amount of a given benzodiazepine compound is within the range of from about 10 percent to about 50 percent of the dosage usually employed to obtain an anxiolytic (anxiety relieving) effect in adult humans.

Benzodiazepine compounds having sedative-hypnotic and anxiolytic (anxiety reducing) properties are a well defined class of compounds which may be broadly characterized as central nervous system depressants. Illustrative of benzodiazepine central nervous system depressants are benzodiazepine compounds of the general formula:

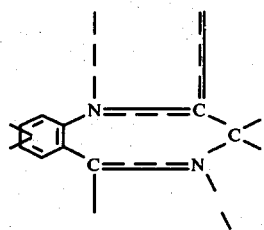

(I)

N-oxides thereof, and their pharmaceutically acceptable acid addition salts, whrein the broken lines are used to indicate alternative covalent bonds. More specifically illustrative of the benzodiazepine compounds which may be used in carrying out the method of the invention are:

1. the 1,4-benzodiazepine 4-oxides of formula:

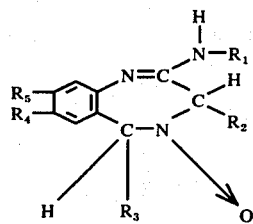

(II)

and their pharmaceutically acceptable acid addition salts wherein $R_1$ represents hydrogen, lower alkyl, lower alkenyl, hydroxy-substituted lower alkyl or lower alkoxy-substituted lower alkyl; $R_2$ represents hydrogen or lower alkyl; $R_3$ represents phenyl, halophenyl, nitrophenyl or lower alkoxyphenyl and $R_4$ and $R_5$ each represent hydrogen, halogen or lower alkyl. The compounds (II) are well known as is their preparation (see, for example, U.S. Pat. No. 2,893,992). Illustrative of the compounds of formula (II) are 7-chloro-2-methylamino-5-phenyl-3H-1,4-benzodiazepine 4-oxide; 7-chloro-2-methylamino-5-phenyl-3H-1,4-benzodiazepine 4-oxide; 7-bromo-2-amino-5-phenyl-3H-1,4-benzodiazepine 4-oxide; and 7-chloro-2-methylamino-5-phenyl-3H-1,5-benzodiazepine 4-oxide hydrochloride and the like which are generally employed in the method of this invention at a dosage of from about 0.01 mg. to about 1.0 mg. per kilogram of body weight of the recipient on a daily basis;

2. the well known 5-monocyclic aryl-1,4-benzodiazepin-2-ones of formula:

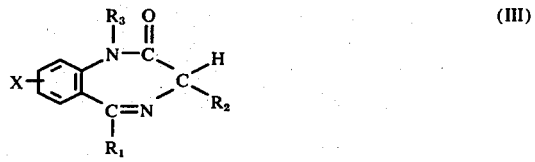

(III)

and the pharmaceutically acceptable acid addition salts thereof wherein $R_1$ is phenyl, halophenyl, pyridyl or thienyl; $R_2$ is hydrogen, hydroxy, lower alkoxy, halogen substituted lower alkoxy, phenoxy, or benzyloxy; $R_3$ is hydrogen or lower alkyl and X is halogen. The compounds (III) are prepared by the methods of U.S. Pat. Nos. 3,136,815; 3,296,249 and Bell et al., J. Org. Chem. 27, 1691, (1962). Illustrative of the compounds of formula (III) are 3-acetoxy-7-chloro-1,3-dihydro-5-phenyl-2H-1,4-benzodiazepin-2-one;

3-acetoxy-1,3-dihydro-5-phenyl-2H-1,4-benzodiazepin-2-one;

3-acetoxy-7-chloro-1,3-dihydro-1-methyl-5-phenyl-2H-1,4-benzodiazepin-2-one;

3-acetoxy-7-bromo-5(p-chlorophenyl)-1,3-dihydro-2H-1,4-benzodiazepin-2-one;

3-acetoxy-7-chloro-1,3-dihydro-5-(2-thienyl)-2H-1,4-benzodiazepin-2-one;

7-chloro-3-(α-chloroacetoxy)-1,3-dihydro-5-phenyl-2H-1,4-benzodiazepin-2-one;

3-benzoxy-7-chloro-1,3-dihydro-5-phenyl-2H-1,4-benzodiazepin-2-one;

7-chloro-1,3-dihydro-3-ethoxy-5-phenyl-2H-1,4-benzodiazepin-2-one;

7-chloro-1,3-dihydro-3-hydroxy-5-phenyl-2H-1,4-benzodiazepin-2-one;

7-chloro-1,3-dihydro-3-hydroxy-1-methyl-5-phenyl-2H-1,4-benzodiazepin-2-one;

7-chloro-5-(o-chlorophenyl)-1,3-dihydro-3-hydroxy-2H-1,4-benzodiazepin-2-one;

7-chloro-5-(o-chlorophenyl)-1,3-dihydro-3-hydroxy-1-methyl-2H-1,4-benzodiazepin-2-one;

7-chloro-1,3-dihydro-1-methyl-5-phenyl-2H-1,4-benzodiazepin-2-one and the like, which may be given according to the method of this invention in doses of from about 0.01 mg. to about 1.0 mg. per kilogram body weight of the recipient on a daily basis;

3. the oxazinobenzodiazepines such as those illustrated by the formula:

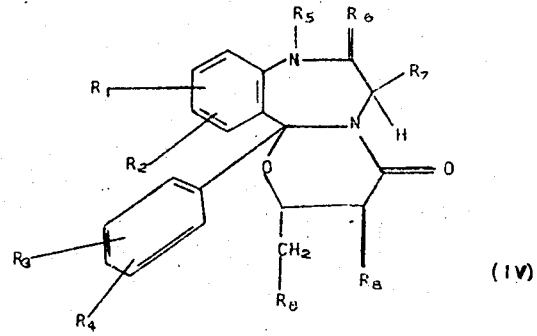

(IV)

wherein $R_1$, $R_2$, $R_3$ and $R_4$ are each selected from hydrogen, alkyl and alkoxy each of 1 to 6 carbon atoms, inclusive, halogen, trifluoromethyl, nitro and cyano; $R_5$ is selected from hydrogen, alkyl of 1 to 6 carbon atoms, inclusive, and benzyl; $R_6$ is selected from the groups =O and =S; $R_7$ is selected from hydrogen, alkyl and alkoxy, each having 1 to 6 carbon atoms, inclusive; and $R_8$ is selected from hydrogen, alkyl of 1 to 6 carbon atoms, inclusive, and phenyl.

The compounds (IV) are well known as is their preparation; see, for example, U.S. Pat. No. 3,573,282. Illustrative of the compounds (IV) are 11-chloro-8,12b-dihydro-2-benzyl-3,12b-diphenyl-8-methyl-4H-[1,3]oxazino-[3,2-d]-[1,4]-benzodiazepine-4,7(6H)-dione;

11-chloro-8,12b-dihydro-2-methyl-12b-phenyl-4H-[1,3]oxazino-[3,2-d][1,4]benzodiazepine-4,7(6H)-dione;

11-trifluoromethyl-8,12b-dihydro-2,8-dimethyl-12b-phenyl-4H-[1,3-]oxazino[3,2-d][1,4]-benzodiazepine-4,7-(6H)-dione;

11-chloro-8,12b-dihydro-2,8-dimethyl-12b-(p-chlorophenyl)-4H-[1,4-]oxazino[3,2-d][1,4]benzodiazepine-4,7-(6H)-dione;

11-cyano-8,12b-dihydro-2,8-dimethyl-12b-phenyl-4H-[1,3]oxazino[3,2-d][1,4]benzodiazepine-4,7(6H)-dione;

11-chloro- 8,12b-dihydro-3-ethyl-8-methyl-2-propyl-12b-phenyl-4H-[1,4]oxazino[3,2-d][1,4]benzodiazepine-4,7(6H)-dione;

11-chloro-8,12b-dihydro-2-ethyl-3,8-dimethyl-12b-phenyl-4H-[1,3]oxazino[3,2-d][1,4]benzodiazepine-4,7-(6H)-dione;

7,12b-dihydro-2,8-dimethyl-12b-phenyl-4H-[1,3]-oxazino[3,2-d][1,4]benzodiazepine-4,7(6H)-dione;
11-nitro-8,12b-dihydro-2,8-dimethyl-12b-(o-fluorophenyl)-4H-[1,3]oxazino[3,2-d][1,4]benzodiazepine-4,7-(6H)-dione;

11nitro-8,12b-dihydro-2,8-dimethyl-12b-phenyl-4H-[1,3]oxazino[3,2-d][1,4]benzodiazepine-4,7(6H)-dione;

11-chloro-8,12b-dihydro-2-isobutyl-3-isopropyl-8-methyl-12b-phenyl-4H-[1,4]oxazino-[3,2-d][1,4]benzodiazepine-4,7(6H)-dione;

11-chloro-8,12b-dihydro-6-methoxy-2,8-dimethyl-12b-phenyl-4H-[1,3]oxazino[3,2-d][1,4]benzodiazepine-4,7-(6H)-dione;

11-fluoro-8,12b-dihydro-2-ethyl-3,8-dimethyl-12b-phenyl-4H-[1,3]oxazino[3,2-d][1,4]benzodiazepine-4,7-(6H)-dione;

11-chloro-8,12b-dihydro-2,8-dimethyl-12b-(o-fluorophenyl)-4H-[1,3]oxazino[3,2-d][1,4]benzodiazepine-4,7-(6H)-dione;

11-chloro-8,12b-dihydro-2,8-dimethyl-12b-(o-chlorophenyl)-4H-[1,3]oxazino[3,2-d][1,4]benzodiazepine-4,7-(6H)-dione;

11-chloro-8-(cyclopropylmethyl)-8,12b-dihydro-2-methyl-12b-phenyl-4H-[1,3]oxazino[3,2-d][1,4]benzodiazepine-4,7(6H)-dione;

11-chloro-8,12b-dihydro-2-pentyl-3-butyl-12b-phenyl-4H-[1,3]-oxazino[3,2-d][1,4]benzodiazepine-4,7(6H)-dione;

9-methoxy-11-iodo-8,12b-dihydro-2-heptyl-3-hexyl-12b-(3,4-dimethylphenyl)-4H-[1,3]oxazino[3,2-d][1,4]-benzodiazepine-4,7-(6H)-dione;

12-chloro-8,12b-dihydro-2-methyl-8-propyl-12b-phenyl-4H-[1,3]-oxazino[3,2-d][1,4]benzodiazepine-4,7-(6H)-dione;

10-trifluoromethyl-8,12b-dihydro-2,8-dimethyl-12b-(p-bromophenyl)-4H-[1,4]oxazino[3,2-d][1,4]benzodiazepine-4,7(6H)-dione;

9-bromo-8,12b-dihydro-2,8-diethyl-3-methyl-12b-(p-tolyl)-4H-[1,3]oxazino[3,2-d][1,4-benzodiazepine-4,7(6H)-dione;

10-nitro-8,12b-dihydro-2-propyl-3-ethyl-12b-phenyl-4H-[1,3]oxazino[3,2-d][1,4]benzodiazepine-4,7(6H)dione;

11-nitro-8,12b-dihydro-2,8-dibutyl-3-propyl-12b-(p-trifluoromethylphenyl)-4H-[1,3]oxazino[3,2-d][1,4-benzodiazepine-4,7(6H)-dione;

9-methyl-10-nitro-8,12b-dihydro-2-methyl-8-benzyl-12b-(3,4-diethoxyphenyl)-4H-[1,4]oxazino[3,2-d][1,4-benzodiazepine-4,7(6H)-dione;

12-bromo-9-butoxy-8,12b-dihydro-2-hexyl-3-pentyl-8-benzyl-12b-(p-propylphenyl)-4H-[1,3]oxazino[3,2-d][1,4]-benzodiazepine-4,7(6H)-dione;

11-chloro-12-nitro-8,12b-dihydro-6-methoxy-2-methyl-12b-(m-bromophenyl)-4H-[1,4]oxazino[3,2-d][1,4benzodiazepine-4,7(6H)-dione;

11-bromo-8,12b-dihydro-6-ethoxy-2-propyl-3-ethyl-8-benzyl-12b-(p-chlorophenyl)-4H-[1,3]oxazino[3,2-d][1,4]-benzodiazepine-4,7(6H)-dione;

9-methyl-8,12b-dihydro-2,6,8-triethyl-3-methyl-12b-(p-iodophenyl)-4H-[1,3]oxazino[3,2-d][1,4]benzodiazepine-4,7(6H)-dione;

10-cyano-8,12b-dihydro-2-methyl-6,8-dibutyl-12b-phenyl-4H-[1,3]oxazino[3,2-d][1,4]benzodiazepine-4(6H)-one- 7-thione;

9-cyano-8,12b-dihydro-2-butyl-3-propyl-8-benzyl-12b-(m-butylphenyl)-4H-[1,3]oxazino[3,2-d][1,4]benzodiazepine-4(6H)-one-7-thione;

11-fluoro-8,12b-dihydro-2-pentyl-3-butyl-8-methyl-12b-(m-trifluoromethylphenyl)-4H-[1,3]oxazino[3,2-d][1,4]-benzodiazepine-4(6H)-one-7-thione, and the like. Generally the compounds (IV) are given according to the method of this invention in doses of from about .01 mg. to about 1.0 mg. per kilogram of body weight of the recipient on a daily basis;

4. the 2,4-dihydro-6-phenyl-1H-s-triazolo-[3,2-a][1,4]benzodiazepine-1-one compounds of formula:

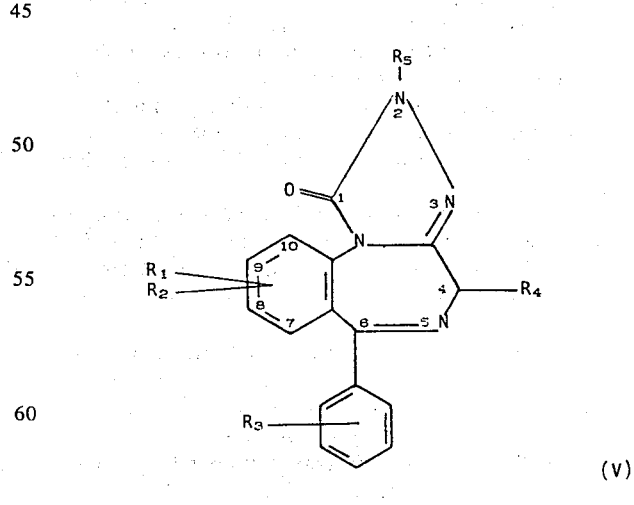

(V)

and the pharmaceutically acceptable acid addition salts thereof wherein $R_1$, $R_2$ and $R_3$ are each selected from the group consisting of hydrogen, lower alkyl, halogen, nitro, cyano, trifluoromethyl, lower alkoxy, alkylthio, alkylsulfinyl, alkylsulfonyl, alkanoylamino and dialkylamino, in which the carbon chain moieties in each instance are of 1 to 3 carbon atoms, inclusive, and wherein $R_4$ and $R_5$ are selected from the group consisting of hydrogen and lower alkyl.

The compounds (V) are well known as is their preparation; see, for example, U.S. Pat. No. 3,708,592. Illustrative of the compounds (V) are 2,4-dihydro-6-phenyl-8-chloro-1H-s-triazolo-[4,3-a][1,4]benzodiazepin-1-one;

2,4-dihydro-2-methyl-6-phenyl-8-chloro-1H-s-triazolo[3,2-a][1,4]benzodiazepin-1-one;

2,4-dihydro-4-methyl-6-(o-chlorophenyl)-8-chloro-1H-s-triazolo[3,2-a][1,4]benzodiazepin-1-one;

2,4-dihydro-2,4-dimethyl-6-(o-chlorophenyl)-8-chloro-1H-s-triazolo[3,2-a][1,4]benzodiazepin-1-one;

2,4-dihydro-2-methyl-6-(o-chlorophenyl)-8-chloro-1H-s-triazolo[4,3-a][1,4]benzodiazepin-1-one;

2,4-dihydro-6-(o-chlorophenyl)-8-chloro-1H-s-triazolo[4,3-a][1,4]benzodiazepin-1-one;

2,4-dihydro-2-methyl-6-phenyl-8-chloro-1H-s-triazolo[4,3-a][1,4]benzodiazepin-1-one hydrochloride and the like, which are given according to the method of this invention on a dosage schedule of from .001 mg. to about 0.1 mg. per kilogram of body weight of the recipient on a daily basis;

5. the triazolobenzodiazepines of the formula:

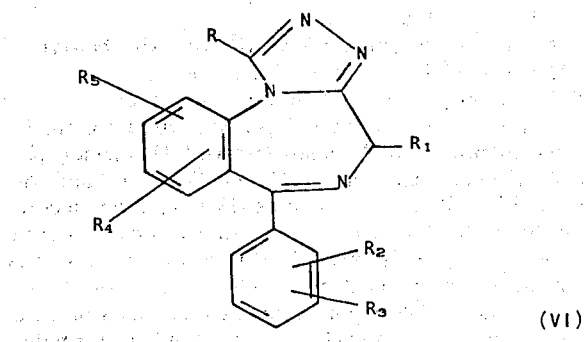

(VI)

wherein R is selected from the group consisting of hydrogen, halogen, cyano, lower alkoxy and lower alkyl; $R_1$ is hydrogen or lower alkyl; $R_2$, $R_3$, $R_4$ and $R_5$ are each selected from the group consisting of hydrogen, lower alkyl, fluorine, chlorine, bromine, nitro, cyano, trifluoromethyl, lower-alkoxyamino, alkanoylamino in which the alkanoyl group is of 1 to 3 carbon atoms, inclusive, lower-alkylthio, lower-alkylsulfinyl and lower-dialkylamino.

The compounds (VI) are well known as is their preparation; see, for example U.S. Pat. Nos. 3,709,898 and 3,709,899. Illustrative of the compounds (VI) are 7-chloro-1-methyl-5-phenyl-s-triazolo[4,3a]-quinoline;

9-(dipropylamino)-1-chloro-6-[p-(dipropylamino)phenyl]-4H-s-triazolo[4,3-a][1,4]benzodiazepine;

7-(ethylsulfonyl)-6-(o-cyanophenyl)-4H-s-triazolo[4,3-a][1,4]benzodiazepine-1-carbonitrile;

4-propyl-1-methoxy-6-[m-(methylthio)phenyl]4H-s-triazolo[4,3-a][1,4]benzodiazepine;

10-fluoro-7-chloro-1-diethylamino-6-[p-(trifluoromethyl)phenyl]4H-s-triazolo[4,3a][1,4]benzodiazepine;

7,9-diethoxy-1-bromo-6-(m-ethoxyphenyl)-4H-s-triazolo[4,3-a][1,4]benzodiazepine;

4-ethyl-1-methoxy-6-[o-(ethylthio)phenyl]-4H-s-triazolo[4,3-a][1,4]benzodiazepine;

4-methyl-7,10-dichloro-1-ethoxy-6-(m-isopropoxyphenyl)-4H-s-triazolo[4,3-a][1,4]benzodiazepine;

9-(dipropylamino)-1-chloro-6-[m-(propylthio)phenyl]-4H-s-triazolo[4,3-a][1,4]benzodiazepine;

7-(diisopropylamino)-1-bromo-6-[p-(dipropylamino)-phenyl]-4H-s-triazolo[4,3-a][1,4]benzodiazepine;

4-isopropyl-7,9-difluoro-1-morpholino-6-phenyl-4H-s-triazolo[4,3-a][1,4]benzodiazepine;

8-chloro-1-piperidino-6-(3,4-dimethylphenyl)-4H-s-triazolo[4,3-a][1,4]benzodiazepine;

6-(2-methyl-4-methoxyphenyl)-4H-s-triazolo[4,3-a]-[1,4]benzodiazepine-1-carbonitrile;

8-methylthio-1-methoxy-6-phenyl-4H-s-triazolo-[4,3-a][1,4]benzodiazepine;

8-methoxy-1-ethoxy-6-phenyl-4H-s-triazolo[4,3-a]-[1,4]benzodiazepine;

1,10-dichloro-6-(m-isopropylphenyl)-4H-s-triazolo[4,3-a][1,4]benzodiazepine;

9-(dipropylamino)-1-bromo-6-[p-(dipropylamino)phenyl]-4H-s-triazolo[4,3-a][1,4]benzodiazepine;

8-(methylsulfinyl)-1-bromo-6-(o-nitrophenyl)-4H-s-triazolo[4,3-a][1,4]benzodiazepine;

7-(ethylsulfonyl)-1-propyloxy-6-(o-cyanophenyl)-4H-s-triazolo[4,3-a][1,4]benzodiazepine;

4-propyl-2-isopropyloxy-6-[m-(methylthio)phenyl]-4H-s-triazolo[4,3-a][1,4]benzodiazepine;

10-fluoro-7-chloro-1-ethoxy-6-[p-(trifluoromethyl)-phenyl]-4H-s-triazolo[4,3-a][1,4]benzodiazepine;

7,9-diethoxy-6-(m-ethoxyphenyl)-4H-s-triazolo-[4,3-a][1,4]benzodiazepine-1carbonitrile;

7-(propylthio)-6-(m-iodophenyl)-4H-s-triazolo-[4,3-a][1,4]benzodiazepine-1-carbonitrile;

1-chloro-4-ethyl-6-[o-(ethylthio)phenyl]-4H-s-triazolo[4,3-a][1,4]benzodiazepine;

7,10-dichloro-1-ethoxy-4-methyl-6-(m-isopropoxyphenyl)-4H-s-triazolo[4,3-a][1,4]benzodiazepine;

9-(dipropylamino)-1-propoxy-6-[m-(propylthio)phenyl]-4H-s-triazolo[4,3-a][1,4]benzodiazepine;

7-(diisopropylamino)-1-chloro-6-[p-(dipropylamino)phenyl]-4H-s-triazolo[4,3-a][1,4]benzodiazepine;

8-chloro-6-(3,4-dimethylphenyl)-4H-s-triazolo-[4,3-a][1,4]benzodiazepine-1-carbonitrile;

6-(2-methyl-4-methoxyphenyl)-4H-s-triazolo-[4,3-a][1,4]benzodiazepine-1-carbonitrile;

8-methylthio-1-bromo-6-phenyl-4H-s-triazolo-[4,3-a][1,4]benzodiazepine;

8-methoxy-1-chloro-6-phenyl-4H-s-triazolo-[4,3-a][1,4]benzodiazepine;

8-chloro-1-pyrrolidino-6-(o-chlorophenyl)-4H-s-triazolo[4,3-a][1,4]benzodiazepine;

8-chloro-1-morpholino-6-(o-nitrophenyl)-4H-s-triazolo[4,3-a][1,4]benzodiazepine;

8-chloro-1-piperidino-6-(2,6-difluorophenyl)-4H-s-triazolo[4,3-a][1,4]benzodiazepine;

1-bromo-8-chloro-6-phenyl-4H-s-triazolo-[4,3-a][1,4]benzodiazepine;

1,8-dichloro-6-phenyl-4H-s-triazolo[4,3-a][1,4]benzodiazepine;

1-cyano-8-chloro-6-phenyl-4H-s-triazolo[4,3-a][1,4]benzodiazepine;

1-methoxy-8-chloro-6-phenyl-4H-s-triazolo[4,3-a][1,4]benzodiazepine;

1-ethoxy-8-chloro-6-phenyl-4H-s-triazolo[4,3-a][1,4]benzodiazepine;

1-dimethylamino-8-chloro-6-phenyl-4H-s-triazolo-[4,3-a][1,4]benzodiazepine;

1-diethylamino-8-chloro-6-phenyl-4H-s-triazolo-[4,3-a][1,4]benzodiazepine;

1-pyrrolidino-8-chloro-6-phenyl-4H-s-triazolo-[4,3-a][1,4]benzodiazepine;

8-chloro-1-methyl-6-(2,6-difluorphenyl)-4H-s-triazolo[4,3-a][1,4]benzodiazepine;

8-chloro-1-ethyl-6-phenyl-4H-s-triazolo[4,3-a][1,4]benzodiazepine;

8-chloro-6-phenyl-4H-s-triazolo[4,3-a][1,4]-benzodiazepine;

8-trifluoromethyl-1-methyl-6-phenyl-4H-s-triazolo-[4,3-a][1,4]benzodiazepine;

8-chloro-1-methyl-6-(o-chlorophenyl)-4H-s-triazolo-[4,3-a][1,4]benzodiazepine;

8-chloro-1-methyl-6-(o-fluorophenyl)-4H-s-triazolo-[4,3-a][1,4]benzodiazepine;

8-chloro-6-phenyl-4H-s-triazolo[4,3-a][1,4]-benzodiazepine;

8-trifluoromethyl-1-methyl-6-phenyl-4H-s-triazolo-[4,3-a][1,4]benzodiazepine;

8-chloro-1-methyl-6-(o-fluorophenyl)-4H-s-triazolo-[4,3-a][1,4]benzodiazepine;

7-(ethylthio)-1-propyl-6-(o-bromophenyl)-4H-s-triazlo[4,3-a][1,4]benzodiazepine;

10-(trifluoromethyl)-6-[p-(propionylamino)phenyl]-4H-s-triazolo[4,3-a][1,4]benzodiazepine;

9-propoxy-8-bromo-1-ethyl-6-[m-(ethylsulfinyl)-phenyl]-4H-s-triazolo[4,3-a][1,4]benzodiazepine;

9-nitro-8-ethyl-1-propyl-6-[o-(ethylsulfinyl)-phenyl]-4H-s-triazolo[4,3-a][1,4]benzodiazepine;

1-methyl-7-fluoro-6-(o-fluorophenyl)-4H-s-triazolo-[4,3-a][1,4]benzodiazepine;

1-isopropyl-6-(p-tolyl)-4H-s-triazolo[4,3-a][1,4]-benzodiazepine;

1-propyl-7,10-dibromo-6-(p-chlorophenyl)-4H-s-triazolo[4,3-a][1,4]benzodiazepine;

1-ethyl-8-amino-6-(p-nitrophenyl)-4H-s-triazolo-[4,3-a][1,4]benzodiazepine;

1-isopropyl-8-fluoro-6-(o-cyanophenyl)-4H-s-triazolo-[4,3-a][1,4]benzodiazepine;

1-isopropyl-8-acetamido-7-chloro-6-(m-aminophenyl)-4H-s-triazolo[4,3-a][1,4]benzodiazepine;

7-dimethylamino-6-[o-(methylsulfinyl)phenyl]-4H-s-triazolo[4,3-a][1,4]benzodiazepine;

8-(propylthio)-1-propyl-6-(p-ethoxyphenyl)-4H-s-triazolo[4,3-a][1,4]benzodiazepine;

9-methyl-6-(o-aminophenyl)-4H-s-triazolo[4,3-a]-[1,4]benzodiazepine;

and the like; which may be given according to the method of this invention on a dosage schedule of from about 0.01 mg. to about 1.0 mg. per kilogram of body weight of recipient on a daily basis;

6. the 5-phenyl-1,3-dihydro-3H-1,4-benzodiazepines of formula:

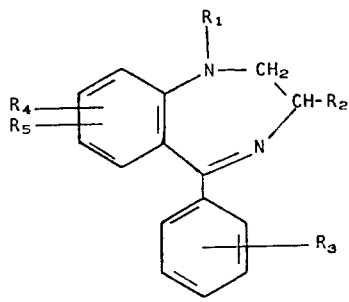

(VII)

and the pharmaceutically acceptable acid addition salts thereof wherein $R_1$ is selected from the group consisting of hydrogen, lower alkyl, lower alkenyl, and lower alkanoyl; $R_2$ is selected from the group consisting of hydrogen and lower alkyl; and $R_3$, $R_4$, and $R_5$ are each selected from the group consisting of hydrogen, halogen, trifluoromethyl, nitro, amino, loweralkanoylamino, lower-alkylthio, lower-alkylsulfonyl, lower-alkylsulfinyl, lower-alkoxy, hydroxy, lower alkyl, cyano, carboxy and di-lower alkylamino.

Compounds of the formula (VII) are well known and are prepared, for example, by the methods disclosed in U.S. Pat. No. 3,109,843 and S. African Pat. No. 62/4889.

Illustrative of the compounds (VII) are 7-chloro-5-phenyl-1,3-dihydro-3H-1,4-benzodiazepine;

7-chloro-1-methyl-5-phenyl-1,3-dihydro-3H-1,4-benzodiazepine;

1-acetyl-7-chloro-5-phenyl-1,2-dihydro-3H-1,4-benzodiazepine;

7-chloro-5-phenyl-1,2,4,5-tetrahydro-3H-benzodiazepine hydrochloride;

5-phenyl-1,2-dihydro-3H-1,4-benzodiazepine;

7-chloro-5-(2-chlorophenyl)-1,2-dihydro-3H-1,4-benzodiazepine;

7-chloro-5-(2-chlorophenyl)-1-methyl-1,2,4,5-tetrahydro-3H-1,4-benzodiazepine;

7-chloro-1,4-dimethyl-1,2,4,5-tetrahydro-5-phenyl-3H-1,4-benzodiazepine;

7-trifluoromethyl-5-phenyl-1,2,dihydro-3H-1,4-benzodiazepine;

7-nitro-5-phenyl-1,2-dihydro-3H-1,4-benzodiazepine;

7-chloro-1,4-dimethyl-5-(2-fluorophenyl)-1,2,4,5-tetrahydro-3H-1,4-benzodiazepine;

7-chloro-1,2,4,5-tetrahydro-5-(3-fluorophenyl)-3H-1,4-benzodiazepine;

7-amino-1-methyl-5-phenyl-1,2-dihydro-3H-1,4-benzodiazepine dihydrochloride;

7-cyano-1-methyl-5-phenyl-1,2-dihydro-3H-1,4-benzodiazepine;

2,3-dihydro-5-phenyl-7-trifluoromethyl-1H-1,4-benzodiazepine;

7-dimethylamino-1-methyl-5-phenyl-1,2-dihydro-3H-1,4-benzodiazepine;

7-bromo-2,3-dihydro-5-phenyl-1H-1,4-benzodiazepine;

7-methylmercapto-5-phenyl-2,3-4-5-tetrahydro-1H-1,4-benzodiazepine;

7-chloro-2,3-dihydro-5-(2-methoxyphenyl)-1H-1,4-benzodiazepine;

7-carboxy-2,3-dihydro-5-phenyl-1H-1,4-benzodiazepine;

4-acetyl-7-chloro-4,5-dihydro-1-ethyl-5-(2-fluorophenyl)-3H-1,4-benzodiazepine and the like.

The compounds (VII) may be given according to the method of this invention on a dosage schedule of about 0.01 mg. to about 1.0 mg. per kilogram of body weight of the recipient on a daily basis;

7. the 3-alkyl-7-phenylpyrimido [1,2-a][1,4]-benzodiazepin-1[5H]-one compounds of formula:

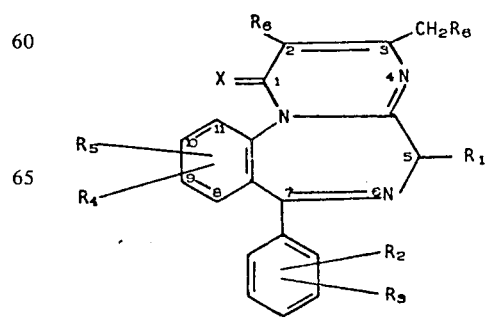

(VIII)

and their pharmaceutically acceptable acid addition salts, wherein $R_1$ is hydrogen, lower alkyl, hydroxy or acetoxy; $R_2$, $R_3$, $R_4$ and $R_5$ are each selected from hydrogen, halogen, nitro, cyano, trifluoromethyl, sulfonamido, amino, alkyl, alkoxy, alkylthio, alkylsulfinyl, alkylsulfonyl, alkanoylamino or dialkylamino in which the carbon moiety is of 1 to 3 carbon atoms, inclusive per alkane radical; $R_6$ is hydrogen, lower alkyl, phenyl or benzyl; and X is oxygen, sulfur or the group =NH.

The compounds (VIII) are well known as is their preparation; see, for example U.S. Pat. No. 3,734,912. Illustrative of the compounds (VIII) are 9-chloro-3-methyl-7-phenylpyrimido[1,2-a][1,4]-benzodiazepin-1(5H)-one;

3-methyl-9-nitro-7-phenylpyrimido[1,2-a][1,4]-benzodiazepin-1(5H)-one;

9-chloro-3-methyl-7-phenylpyrimido[1,2-a][1,4]-benzodiazepin-1-(5H)-thione and the like, all of which may be given according to the method of this invention on a dosage schedule of from about 0.001 mg. to about 0.1 mg. per kilogram of body weight of the recipient on a daily basis.

Preferred benzodiazepines for use in the method of the invention are those of group (2.) above having the formula (III). Most preferred is 7-chloro-1,3-dihydro-1-methyl-5-phenyl-2H-1,4-benzodiazepin-2-one.

As used herein, the term "lower alkyl" means alkyl of 1 to 3 carbon atoms, inclusive. The term "lower alkenyl" means alkenyl of 1 to 3 carbon atoms, inclusive. The term "hydroxy-substituted lower alkyl" means lower alkyl as previously defined wherein a hydrogen atom has been replaced with a hydroxy group. The term "lower alkoxy-substituted lower alkyl" means lower alkyl as defined above wherein a hydrogen atom has been replaced with a lower alkoxy group of formula:

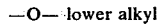
—O— lower alkyl

The term "lower alkoxyphenyl" is used herein to mean phenyl wherein a hydrogen atom has been replaced with a lower alkoxy group as shown above. The term "halogen" is used in its conventional sense as embracive of chlorine, bromine, iodine and fluorine.

The term "halogen-substituted lower alkoxy" means lower alkoxy as defined above wherein a hydrogen atom has been replaced with a halogen atom. The term "phenoxy" means the moiety of formula:

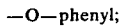
—O—phenyl;

and the term "benzyloxy" means the moiety of formula:

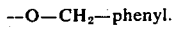
—O—CH₂—phenyl.

The term "alkylthio" is used herein to mean the moiety of formula:

—S—alkyl wherein alkyl has the stated carbon content. The term "alkylsulfinyl" means the moiety of formula —SO—alkyl; wherein alkyl has the stated carbon content. The term "alkylsulfonyl" as used herein means the moiety of formula:

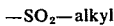
—SO₂—alkyl wherein alkyl has the stated carbon content; and the term "dialkylamino" means the monovalent moiety of formula:

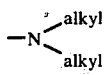

wherein alkyl has the stated carbon content. The term "lower alkanoyl" as used herein means the group of formula:

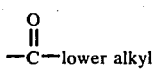

wherein lower alkyl is as defined above.

The benzodiazepine compounds may be administered according to the method of the invention in their conventionally available pharmaceutical dosage forms. Such dosage forms are well known and are represented by capsules, tablets, powders, granules, syrups, dispersions, suspensions, parenteral solutions, injectable suspensions, suppositories and like dosage forms.

Preferably, the benzodiazepine compound is compounded with the 3,4-dihydroxyphenyl-1-alanine or a hydrate or an acid addition salt thereof in an orally administrable dosage form, to obtain a composition of the invention. Thus compositions of the invention comprise solid and liquid pharmaceutical preparations containing potentiating amounts of benzodiazepines and effective amounts of 3,4-dihydroxyphenyl-1-alanine or a hydrate or an acid addition salt thereof in such proportions that together they constitute the essential active ingredients for alleviating the symptoms of paralysis agitans in humans. The solid oral compositions may be in the form of tablets, scored or unscored, coated and uncoated; capsules, hard and soft; powders; granules; pills; (enteric coated tablets, capsules or pills); and the like. Solid diluents and carriers for solid oral compositions of the invention are those conventionally employed for such compositions and are selected from the group consisting of lipids, carbohydrates, proteins and mineral solids, for example starch, sucrose, kaolin, dicalcium phosphate, gelatin, acacia, corn syrup, corn starch, talc and the like.

Tablets contain the essential active ingredients in the required amount with pharmaceutically acceptable diluents, excipients, binders, disintegrators and lubricants. The essential active ingredients are preferably mixed with a carbohydrate diluent, for example starch and lactose; a mineral solid, for example, terra alba (calcium sulfate) and dicalcium phosphate or the like, to form a basic powder mixture. The said mixture may be granulated by wetting with a protein binder such as gelatin solution, a carbohydrate such as starch paste, syrup, or acacia mucilage; and screened. As an alternative to granulating, the mixture may be slugged and the slugs broken down into granules prior to formation of the tablets. A carbohydrate disintegrator, for example corn starch, is advantageously added at the time of forming the basic mixture. A lubricant, for example a lipid such as stearic acid, a stearate salt and mineral oil; a mineral solid such as talc; and the like, is used to prevent sticking of the mixture to the tablet-forming dies. The tablets may be coated or uncoated. Coatings may be a sealing coat of shellac, a taste-disguising carbohydrate coating such as sugar and methyl cellulose or a lipid polish coating of, for example, carnauba wax. Coatings may also comprise (a) lipid type coatings of a semi-permeable nature for delaying absorption of the essential active ingredients to provide sustained action, or (b) enteric substances such as styrene maleic acid copolymer and cellulose acetate phthalate to resist release of the essential active ingredients in the stomach and permit release in the upper intestine.

Capsules for oral use comprise the essential active ingredients in combination with a pharmaceutically acceptable diluent or excipient and a formed gelatin enclosure for the composition. The capsules may be in the form of soft capsules enclosing the active ingredients in the required amount with suitable diluents, for example edible oils. The diluents for hard capsules comprise mineral solids, for example talc, dicalcium phosphate, and the like; carbohydrates, for example starch and lactose and, as required, lubricants, for example stearate salts.

Powders may be advantageously and conveniently prepared by comminuting the essential active ingredients in the required amount and mixing with a pharmaceutically acceptable diluent; for example an edible carbohydrate such as starch, advantageously including sweetening and flavoring agents, for example sugar or flavoring oils.

Liquid oral compositions of the invention may be in the form of dispersions, suspensions, elixirs, and syrups.

Dispersions may be prepared in glycerol, propylene glycol, liquid polyethylene glycols, and mixtures thereof, and in edible oils. Under ordinary conditions of storage and use such preparations contain a preservative to prevent the growth of microorganisms. Likewise, sweetening, coloring, and flavoring agents may be added.

Suspensions are prepared in an aqueous vehicle containing diluents, flavors and preservatives as desired. Advantageously the suspensions contain suspending agents, for example, sodium carboxymethylcellulose, methylcellulose, acacia, polyvinyl pyrrolidone, polyvinyl alcohol and the like.

Syrup compositions of the invention contain the essential active ingredient in the required amount in an aqueous medium containing a sweetening agent, for example, sugar. Colors, flavors and preservatives are added for convenient storage and use.

It is especially advantageous to compound the compositions of the invention in unit dosage form for ease of administration and uniformity of dosage.

The term "dosage unit form" as used in this specification and in the claims refers to physically discrete units suitable as unitary dosages for human subjects, each unit containing a predetermined quantity of the essential active ingredients, ie; an effective amount of 3,4-dihydroxyphenyl-1-alanine for treating paralysis agitans and a potentiating amount of a benzodiazepine as illustrated above, calculated to produce the desired effect in combination with the required pharmaceutical means which adapt said ingredient for systemic administration. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 100 mg. to about 500 mg. of 3,4-dihydroxyphenyl-1-alanine and a hydrate or an acid addition salt thereof and from about 0.5 mg. to about 5 mg. of benzodiazepine potentiator per dosage unit form as the essential active ingredients. The number of units given in treating specific cases of paralysis agitans must be, of course, related to a number of variables such as age, sex and patient involved. The response of a given patient is readily observed and the physician may adjust dosage frequency according to his observations of response, side effects, and like considerations considering the nature of the disease being treated.

When desired, other active ingredients normally employed in treating paralysis agitans, such as, for example apomorphine, may also be compounded with the pharmaceutical compositions of the invention.

The following examples set forth the best mode contemplated by the inventors of making and using the invention but are not to be construed as limiting.

EXAMPLE 1

Oral Tablets

One thousand oral tablets, each containing 250 mg. of 3,4-dihydroxyphenyl-1-alanine and 5 mg. of 7-chloro-1,3-dihydro-1-methyl-5-phenyl-2H-1,4-benzodiazepin-2-one are prepared as follows:

| | |
|---|---|
| 3,4-dihydroxyphenyl-1-alanine | 250 gm. |
| 7-chloro-1,3-dihydro-1-methyl-5-phenyl-2H-1,4-benzodiazepin-2-one | 5 gm. |
| lactose | 200 gm. |
| microcrystalline cellulose NF | 50 gm. |
| starch | 5 gm. |
| magnesium stearate powder | 1 gm. |

The ingredients are thoroughly mixed and slugged. The slugs are broken down by forcing through a screen and the resulting granules are then compressed into tablets.

From one to four of the above tablets may be given one to four times daily to an adult suffering from paralysis agitans. During the course of treatment, alkinesia symptoms are ameliorated.

EXAMPLE 2

Oral Hard-filled Capsules

One thousand two-piece hard gelatin capsules for oral use, each capsule containing 500 mg. of 3,4-dihydroxyphenyl-1-alanine and 5.0 mg. of 7-chloro-1,3-dihydro-1-methyl-5-phenyl-2H-1,4-benzodiazepin-2-one are prepared from the following ingredients:

| | |
|---|---|
| 3,4-dihydroxyphenyl-1-alanine | 500 gm. |
| 7-chloro-1,3-dihydro-1-methyl-5-phenyl-2H-1,4-benzodiazepin-2-one | 5 gm. |
| lactose | 200 gm. |
| talc | 25 gm. |
| magnesium stearate | 2 gm. |

The finely powdered materials are mixed thoroughly then filtered into hard gelatin capsules of appropriate size.

A satisfactory clinical response is obtained in adults suffering from paralysis agitans when given one to four of the above capsules one to four times a day.

EXAMPLE 3

Soft Elastic Capsules

One-piece soft elastic capsules for oral use, each containing 250 mg. of 3,4-dihydroxyphenyl-1-alanine and 5 mg. of 7-chloro-1,3-dihydro-1-methyl-5-phenyl-2H-1,4-benzodiazepin-2-one as the essential active ingredients are obtained by first dispersing the active ingredients in sufficient corn oil to render the material capsulatable and then encapsulating an appropriate volume in gelatin by conventional methods.

One to four capsules given two to four times daily is useful in the treatment of moderate paralysis agitans in humans.

EXAMPLE 4

An aqueous oral preparation containing in each teaspoonful (5 ml.) 250 mg. of 3,4-dihydroxyphenyl-1-alanine and 5 mg. of 7-chloro-1,3-dihydro-1-methyl-5-phenyl-2H-1,4-benzodiazepin-2-one is prepared from the following:

| | |
|---|---|
| 3,4-dihydroxyphenyl-1-alanine | 250 gm. |
| 7-chloro-1,3-dihydro-1-methyl-5-phenyl-2H-1,4-benzodiazepin-2-one | 5 gm. |
| glycerin | 2,000 ml. |
| tragacanth powder | 50 gm. |
| propylparaben | 3.0 gm. |
| sucrose | 6.5 gm. |
| orange oil flavor | 5.0 gm. |
| deionized water q.s. | 5,000 ml. |

The above suspension, when given on a dosage schedule of one to two teaspoonfuls, two to four times daily, to a patient suffering from paralysis agitans, ameliorates symptoms of akinesia.

EXAMPLE 5

Suppositories

One thousand suppositories, each weighing 2.0 gms. and containing 250 mg. of 3,4-dihydroxyphenyl-1-alanine with 5 mg. of 7-chloro-1,3-dihydro-1-methyl-5-phenyl-2H-1,4-benzodiazepin-2-one are prepared from the following ingredients:

| | |
|---|---|
| 3,4-dihydroxyphenyl-1-alanine | 250 gm. |
| 7-chloro-1,3-dihydro-1-methyl-5-phenyl-2H-1,4-benzodiazepin-2-one | 5 gm. |
| polyethylene glycol 1540 | 500 gm. |
| polyethylene glycol 6000 | 1,000 gm. |
| polyethylene glycol 400 | 250 gm. |

Suspend the active ingredients in the polyethylene glycols on a steam bath and pour, with stirring, into molds and allow to congeal.

These suppositories are useful in alleviating symptoms of paralysis agitans when administered rectally at a dose schedule of one suppository given three times a day.

EXAMPLE 6

Similarly, following the procedures of Examples 1–5 supra., but replacing the benzodiazepine active ingredient as used therein with potentiating amounts of other compounds having one of the formulae II–VIII, supra., as illustrated previously, therapeutic compositions are obtained having use in the alleviation of the symptoms of paralysis agitans when administered to humans afflicted with such disease.

We claim:

1. A method of treatment of paralysis agitans comprising administering from about 250 mg. to about 500 mg. of a compound selected from the group consisting of 3,4-dihydroxyphenyl-1-alanine, a hydrate thereof, or a pharmaceutically acceptable acid addition salt thereof and the coadministering of a potentiating dose of a member selected from the group consisting of 7-chloro-2-methylamino-5-phenyl-3H-1,4-benzodiazepine-4-oxide and a compound of the formula:

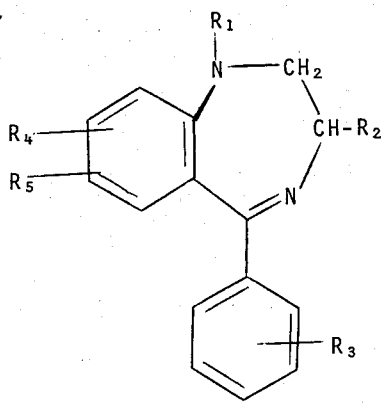

and the pharmaceutically acceptable acid addition salts thereof wherein $R_1$ is selected from the group consisting of hydrogen, lower alkyl, lower alkenyl, and lower alkanoyl; $R_2$ is selected from the group consisting of hydrogen and lower alkyl; and $R_3$, $R_4$, and $R_5$ are each selected from the group consisting of hydrogen, halogen, trifluoromethyl, nitro, amino, lower-alkanoylamino, lower-alkylthio, lower-alkylsulfonyl, lower-alkylsulfinyl, lower-alkoxy, hydroxy, lower alkyl, cyano, carboxy and di-lower alkylamino.

2. A unit dose pharmaceutical composition which consists essentially of from about 250 mg. to about 500 mg. of a compound selected from the group consisting of 3,4-dihydroxyphenyl-1-alanine, a hydrate thereof, or a pharmaceutically acceptable acid addition salt thereof and from about 1 mg. to about 5 mg. of a member selected from the group consisting of 7-chloro-2-methylamino-5-phenyl-3H-1,4-benzodiazepine-4-oxide and a compound of the formula:

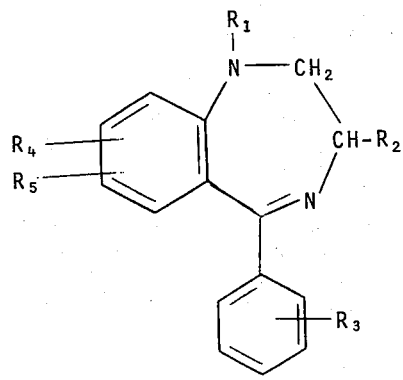

and the pharmaceutically acceptable acid addition salts thereof wherein $R_1$ is selected from the group consisting of hydrogen, lower alkyl, lower alkenyl, and lower alkanoyl; $R_2$ is selected from the group consisting of hydrogen and lower alkyl; and $R_3$, $R_4$, and $R_5$ are each selected from the group consisting of hydrogen, halogen, trifluoromethyl, nitro, amino, lower-alkanoylamino, lower-alkylthio, lower-alkylsulfonyl, lower-alkylsulfinyl, lower-alkoxy, hydroxy, lower alkyl, cyano, carboxy and di-lower alkylamino.

* * * * *